(12) United States Patent
Kunz et al.

(10) Patent No.: US 11,091,566 B2
(45) Date of Patent: Aug. 17, 2021

(54) METHODS FOR THE PRODUCTION OF BIOPOLYMERS WITH DEFINED AVERAGE MOLECULAR WEIGHT

(71) Applicant: MEDSKIN SOLUTIONS DR. SUWELACK AG, Billerbeck (DE)

(72) Inventors: Michael Kunz, Münster (DE); Fabian Kuhlmann, Rosendahl (DE); Claudia Elsinghorst, Billerbeck (DE)

(73) Assignee: MEDSKIN SOLUTIONS DR. SUWELACK AG, Billerbeck (DE)

( * ) Notice: Subject to any disclaimer, the term of this patent is extended or adjusted under 35 U.S.C. 154(b) by 0 days.

(21) Appl. No.: 15/118,269

(22) PCT Filed: Feb. 6, 2015

(86) PCT No.: PCT/EP2015/052540
§ 371 (c)(1),
(2) Date: Aug. 11, 2016

(87) PCT Pub. No.: WO2015/124445
PCT Pub. Date: Aug. 27, 2015

(65) Prior Publication Data
US 2016/0355611 A1 Dec. 8, 2016

(30) Foreign Application Priority Data

Feb. 19, 2014 (EP) .................................... 14155840

(51) Int. Cl.
| | | |
|---|---|---|
| *A61K 31/728* | (2006.01) |
| *A61K 33/38* | (2006.01) |
| *A61K 8/02* | (2006.01) |
| *A61K 8/35* | (2006.01) |
| *A61K 8/37* | (2006.01) |
| *C08B 37/08* | (2006.01) |
| *C08B 37/00* | (2006.01) |
| *A61K 8/73* | (2006.01) |
| *A61K 31/726* | (2006.01) |
| *A61K 31/715* | (2006.01) |
| *A61Q 19/08* | (2006.01) |
| *A61K 31/737* | (2006.01) |
| *C08H 1/06* | (2006.01) |
| *A61K 8/92* | (2006.01) |
| *A61K 9/19* | (2006.01) |
| *A61Q 17/04* | (2006.01) |
| *C08B 3/22* | (2006.01) |
| *A61K 47/36* | (2006.01) |

(52) U.S. Cl.
CPC .......... *C08B 37/0072* (2013.01); *A61K 8/022* (2013.01); *A61K 8/35* (2013.01); *A61K 8/37* (2013.01); *A61K 8/375* (2013.01); *A61K 8/735* (2013.01); *A61K 8/922* (2013.01); *A61K 9/19* (2013.01); *A61K 31/715* (2013.01); *A61K 31/726* (2013.01); *A61K 31/728* (2013.01); *A61K 31/737* (2013.01); *A61K 33/38* (2013.01); *A61Q 17/04* (2013.01); *A61Q 19/08* (2013.01); *C08B 3/22* (2013.01); *C08B 37/0018* (2013.01); *C08B 37/0045* (2013.01); *C08B 37/0063* (2013.01); *C08B 37/0084* (2013.01); *C08B 37/0087* (2013.01); *C08H 1/06* (2013.01); *A61K 47/36* (2013.01)

(58) Field of Classification Search
CPC ... C08B 37/0072; C08B 3/22; C08B 37/0018; C08B 37/0045; C08B 37/0084; C08B 37/0087; C08B 1/06; A61K 8/022; A61K 8/35; A61K 8/37; A61K 8/375; A61K 8/735; A61K 9/19; A61K 31/726; A61K 31/728; A61K 31/737; A61K 33/38; A61K 47/36; A62K 8/922; A61Q 17/04; A61Q 19/08; C08H 1/06
See application file for complete search history.

(56) References Cited

FOREIGN PATENT DOCUMENTS

| EP | 0138572 | A2 | 4/1985 |
| EP | 1987153 | B1 | 11/2008 |
| EP | 1992645 | A1 | 11/2008 |
| EP | 2463309 | B1 | 6/2012 |
| EP | 2479194 | A2 | 7/2012 |
| WO | WO-2007/093179 | A1 | 8/2007 |

OTHER PUBLICATIONS

Wedlock et al. (International Journal of Biological Macromolecules, vol. 5, issue 3, pp. 186-188, published 1982).*
Slovikova, A. et al., Preparation and Modification of collagen-based porous scaffold for tissue engineering. Chemical Papers. 2008; 62(4):417-22.
Tokita, Y. et al., Degradation of hyaluronic acid during freeze drying. Polymer Degradation and Stability. 1997; 55(2):159-64.

(Continued)

*Primary Examiner* — Alma Pipic
(74) *Attorney, Agent, or Firm* — Ballard Spahr LLP

(57) ABSTRACT

The present invention relates to a method for the production of a biopolymer, wherein the biopolymer has a defined average molecular weight, the method comprising lyophylizing a composition comprising the biopolymer with native high molecular weight, optionally purifying and/or isolating the biopolymer; wherein the temperature during the sublimation process is selected to facilitate a controlled and defined degradation of said biopolymer.

9 Claims, 13 Drawing Sheets

(56) References Cited

OTHER PUBLICATIONS

Figure 1:
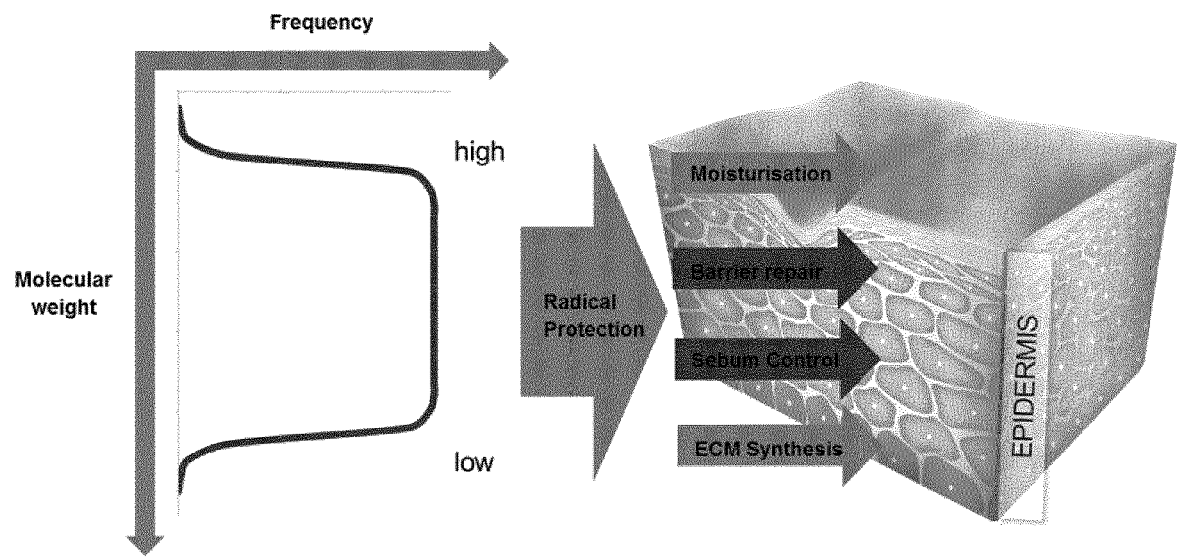

International Search Report and Written Opinion dated Mar. 5, 2015 for International Patent Application No. PCT/EP2015/052540, which was filed on Feb. 6, 2015 and published as WO 2015/124445 on Aug. 27, 2015 (Inventor—Kunz et al.; Applicant—Medskin Solutions Dr. Suwelack AG) (10 pages).

International Preliminary Report on Patentability dated Aug. 23, 2016 for International Patent Application No. PCT/EP2015/052540, which was filed on Feb. 6, 2015 and published as WO 2015/124445 on Aug. 27, 2015 (Inventor—Kunz et al.; Applicant—Medskin Solutions Dr. Suwelack AG) (5 pages).

\* cited by examiner

METHODS FOR THE PRODUCTION OF BIOPOLYMERS WITH DEFINED AVERAGE MOLECULAR WEIGHT

CROSS REFERENCE TO RELATED APPLICATIONS

This application is a U.S. national phase application of International Application No. PCT/EP2015/052540, filed Feb. 6, 2015, and which claims the benefit of European Application No. 14155840.3, filed Feb. 19, 2014. The content of these earlier filed applications are hereby incorporated by reference herein in their entirety.

FIELD OF THE INVENTION

The present invention is in the field of dermatology, pharmaceutics and cosmetics. In particular the invention is in the field of the production of pharmaceutically, dermatologically or cosmetically applicable substances and in the use and application thereof.

BACKGROUND

Biopolymers, such as collagen, polysaccharides or hyaluronic acid are commonly used in cosmetic or dermatological compositions. In many cases these biopolymers are used as moisturizers or anti-oxidants. Common forms of administration are as cream, serum, patches, masks, balms, liquids or as an ointment.

Hyaluronic acid or hyaluronan for example is a biopolymer, which is widely distributed among the human tissue. It is an anionic, non-sulfated glycosaminoglycan comprising the following structure:

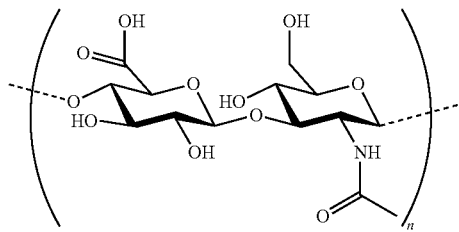

Hyaluronic acid has several medical uses, in particular in dermatology, and is commonly used in cosmetic products, in particular so called anti-ageing products.

In general the bioactivity of biopolymers, such as hyaluronic acid is directly dependent on the average molecular weight of said biopolymers. Taking hyaluronic acid and its use in dermatology for example, the average molecular weight determines the depth of skin penetration and the potential dermatological effects of hyaluronic acid (see FIG. 1).

It is known, that the biological functionality of biopolymers is dependent on their average molecular weight, several methods have been developed to generate biopolymers with defined average molecular weight.

EP 2 479 194 A2 describes the hydrolysis of hyaluronic acid on activated charcoal. EP 2 463 309 B1 and EP 1 992 645 A1 describe several methods for the acidic hydrolysation of hyaluronic acid. Other methods involve the use of enzymatic hydrolysis and filtration (EP 0 138 572 B1) or the use of high temperatures and strong shearing forces (EP 1 987 153 B1).

The problem with all these methods is, that in particular hyaluronic acid needs extensive purification steps to remove the low molecular weight hyaluronic acids, which can be pro-inflammatory.

It is therefore necessary to provide a method for the efficient production of pure biopolymers with defined molecular weight distribution, in particular hyaluronic acid, which allows the control of the average molecular weight of the biopolymer and does not need any further additional purification steps.

BRIEF DESCRIPTION OF THE INVENTION

The present invention relates to a method for the production of a biopolymer, wherein the biopolymer has a defined average molecular weight, the method comprising
(i) lyophilizing a composition comprising the biopolymer,
(ii) optionally purifying and/or isolating the biopolymer,
wherein the temperature during the lyophilization process is selected to facilitate a controlled and defined degradation of said biopolymer.

In a preferred embodiment the invention relates to a method for the production of a biopolymer, wherein the biopolymer has a defined average molecular weight, the method comprising
(i) providing a composition comprising a biopolymer, wherein optionally the pH of the composition has been adjusted to between pH 1.5 and 8.5;
(ii) lyophilizing a composition comprising the biopolymer with native high molecular weight, wherein the lypholization temperature is between −40° C. and 150° C.
(iii) optionally purifying and/or isolating the biopolymer, wherein the temperature during the lyophilization process is selected to facilitate a controlled and defined degradation of said biopolymer.

The invention further relates to the use of said method for the production of biopolymers and to biopolymers, which are produced by said method.

In another embodiment the invention relates to a method for the production of compositions, comprising a biopolymer, wherein the biopolymer has a defined average molecular weight, the method comprising:
(i) providing a base composition comprising a biopolymer,
(ii) lyophilizing said composition;
wherein the temperature during the sublimation process is selected to facilitate a controlled and defined degradation of the biopolymer.

The invention further relates to the use of said method for the production of compositions comprising a biopolymer and to compositions produced by said method.

DEFINITIONS

In the context of the present invention, biopolymers are polymers produced by living organisms. The present invention only relates to native high molecular weight biopolymers, which are preferably not technically or chemically modified, besides the common and native modifications, which occur in the living organism. As polymers, they are characterized by repetitive monomeric motives.

In general biopolymers are divided into three main classes: polynucleotides, polypeptides and polysaccharides. Within the context of this invention the term "biopolymer" only refers to polypeptides and polysaccharides. In the present invention the term "biopolymer" encompasses all naturally occurring modifications of biopolymers, e.g. glycosylation, partial hydrolysis or the attachment of lipids to polypeptides.

Polymers consisting of biological units, but not produced in a living organism, such as polylactic acid, are not considered biopolymers within the meaning of the invention. Biopolymers according to the above mentioned definition processed according to the present invention, are biopolymers in the context of the present invention.

Non-limiting examples for biopolymers according to the present invention comprise: collagens, starch, cellulose derivatives, glucosamino glycans, polysaccarides or fucoidanes.

In the context of the present invention lyophilization or lyophilizing refers to a dehydration process, wherein water is removed by sublimation. Lyophilization is commonly referred to as freeze drying. In general lyophilization comprises three stages:

(i) freezing the composition to be dehydrated, wherein it is important that the composition is cooled below its triple point. The suitable freezing method is dependent on the components of the composition.

(ii) a primary drying phase, in which most of the water is removed, wherein the pressure is lowered to a few µbar or even lower. In this stage the temperature is usually adjusted to get the water sublimated. Preferably, but not necessarily, at this stage the temperature remains under 0° C.

(iii) a secondary drying phase, wherein the pressure is optionally reduced, down to the range of µbar and the temperature preferably raised above 0° C. to remove more strongly bound water.

In one embodiment of the invention, the temperature is controlled during the second drying phase. In another embodiment the temperature is controlled during the primary drying phase. In a particular embodiment the composition is dried using only one drying step, wherein the conditions correspond to the conditions of the second drying step. In an alternative embodiment the composition is dried using only one drying step, wherein the conditions correspond to the conditions of the first drying step.

Within the meaning of the present invention the "temperature during the sublimation process" refers to the temperature of the storage plate on which the composition is placed.

In the context of the present invention the term aqueous solution refers to a solution, wherein the solvent is water. Within the context of the present invention the term further refers to coarse or colloidal suspensions of components, for example non-water-soluble biopolymers or non-soluble cosmetic additions in water.

In the context of the present invention the term emulsion refers to mixtures of normally immiscible liquids. In the context of the present invention the term emulsion in particular refers to water-in-oil or oil-in-water emulsion. Preferably in the context of the present invention the emulsion is stabilized by the use of an emulsifying agent or emulsifier. Non-limited examples for emulsifying agents are lecithin, sodium stearoyl lactylate, polymers with emulsifying functionalities or detergents.

DETAILED DESCRIPTION OF THE INVENTION

The inventors found surprisingly, that biopolymers can be subjected to controlled degradation during lyophilization processes, resulting in biopolymers with defined average molecular weight.

A first aspect of the present invention relates to a method for the production of a biopolymer, wherein the biopolymer has a defined average molecular weight, the method comprising (i) lyophilizing a composition comprising the biopolymer,
(ii) optionally purifying and/or isolating the biopolymer, wherein the maximum temperature during the lyophilization process is selected to facilitate a controlled and defined degradation of said biopolymer.

The composition comprising the biopolymer can be any kind of composition, provided said composition comprises at least small amounts of water in addition to said biopolymer. Said composition may comprise additional biopolymers, i.e. mixtures.

The method is in particular suitable for biopolymers selected from the group comprising hyaluronic acid, collagen, glucosamino glycans, polysaccharides and fucoidanes. In a preferred embodiment the biopolymer is a glucosamino glycan or polysaccarid. In a more preferred embodiment the biopolymer is selected from the group consisting of alginates, rhizobian gum, sodium carboxy methyl cellulose, pullulan, Biosaccharide Gum-1, glucomannane, beta-glucane, pectine, tamarindus indica seed polysaccharide and hyaluronic acid. In an even more preferred embodiment the biopolymer is sodium alginate or hyaluronic acid. In the most preferred embodiment the biopolymer is hyaluronic acid.

In a preferred embodiment the biopolymer is a biopolymer with high molecular weight. In a more preferred embodiment the biopolymer is a biopolymer with native high molecular weight.

In a preferred embodiment the composition comprising the biopolymer is an aqueous solution or an emulsion.

In another embodiment of the present invention the composition comprising the biopolymer is a gel or a liquid with low to high viscosity.

The inventors had found in particular, that controlled conditions during the sublimation process and a control of the parameters of the composition, e.g. salt contents, pH-value, vacuum, used emulsifying agents, allow the control of the average molecular weight of the degraded biopolymer.

In one embodiment of the invention the composition comprising the biopolymer has a pH-value selected from a range between 1.5 and 8.5. In a preferred embodiment the pH value is selected from a range between 2.5 and 6.

Figure 2:
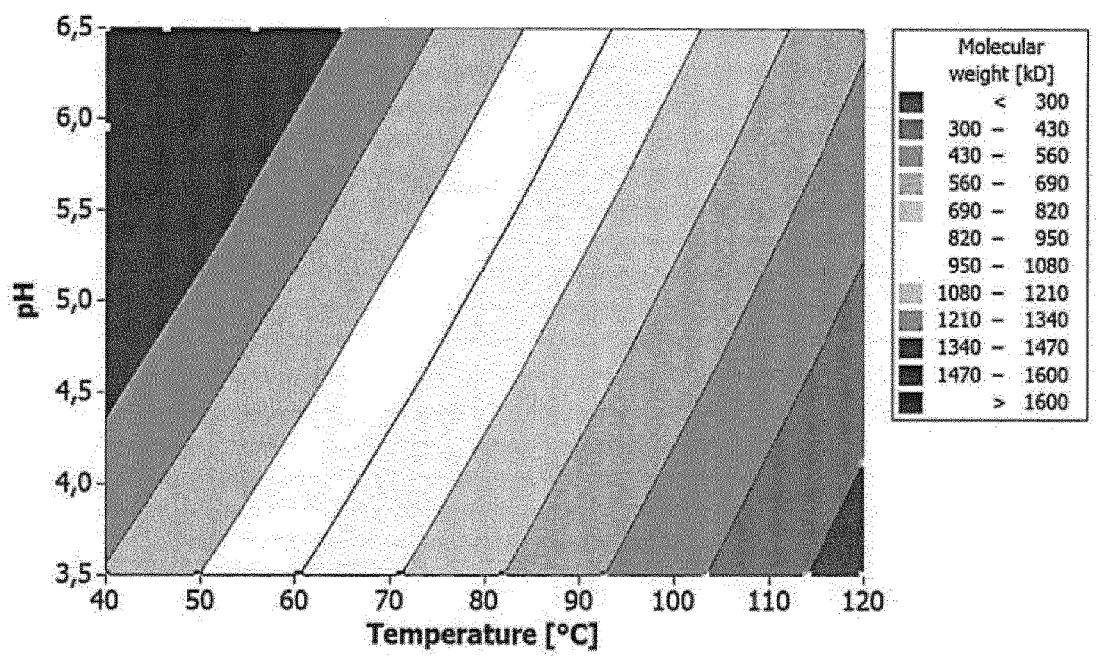

The inventors had found a direct correlation between the pH-value, the temperature during the sublimation process and the average molecular weight of the biopolymer. FIG. 2 shows the correlation found for an analyzed hyaluronic acid.

It is evident that the average molecular weight of the final product of the processed biopolymer is directly dependent on the combination of temperature and pH value selected.

In one embodiment of the invention the maximum temperature during the sublimation process is selected from the range of −40° C. to 150° C. In a preferred embodiment the temperature is selected from the rage of 0 to 140° C. In a more preferred embodiment the temperature is selected from the range of 60 to 130° C. In the most preferred embodiment the temperature is 120° C.

Figure 3:
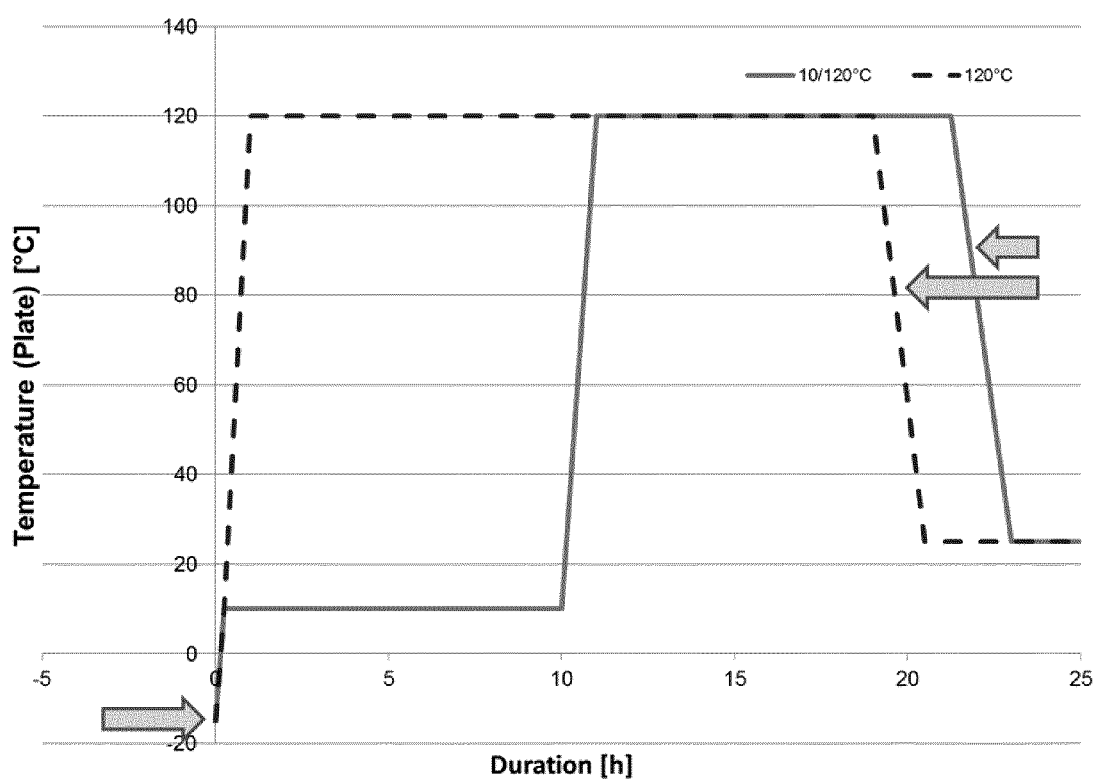

In an alternative embodiment the temperature during the sublimation process is varied during the lyphilization process. In a preferred first embodiment the sublimation is carried out at two temperatures. A schematic overview of preferred temperatures profile is shown in FIG. 3.

In one embodiment of the invention the sublimation process is carried out at two different temperatures. Preferably the first temperature is selected from the range of −30° to +40° C. and the second temperature is selected from the range of 60 to 130° C. In a preferred embodiment the first temperature is selected from the range of −20 to 20° C. and the second temperature is selected from the range of 80 to 120° C. In a most preferred embodiment the first temperature is 10° C. and the second temperature is 120° C.

In an alternative embodiment the temperature profile comprises more than two different temperatures. In an alternative embodiment the temperature profile comprises a continuous temperature gradient.

In one embodiment of the invention the pressure during the sublimation step is between 50 μbar and 800 μbar. In a preferred embodiment of the invention the pressure is between 75 μbar and 600 μbar, more preferably between 100 μbar and 400 μbar, even more preferably between 150 μbar and 300 μbar. In a most preferred embodiment the pressure during the sublimation step is 300 μbar.

The biopolymers produced with the process might be purified or isolated from the composition, however it is preferred that no further purification or isolation step is performed. In the most preferred embodiment the biopolymer is directly suitable for further processing and/or use.

The present invention does not only relate to a method for the production of biopolymers with defined average molecular weight, but also to the use of said method for the production of biopolymers with defined average molecular weight and to the biopolymers with defined average molecular weight produced with said method.

In a preferred embodiment the method is used for the productions of biopolymers with defined average molecular weight, which are selected from the group comprising hyaluronic acid, collagen, glucosamino glycans, polysaccharides and fucoidanes. In a more preferred embodiment the biopolymer is a glucosamino glycan. In a more preferred embodiment the method is used for the productions of biopolymers with defined average molecular weight selected from alginates, rhizobian gum, sodium carboxy methyl cellulose, pullulan, Biosaccharide Gum-1, glucomannane, beta-glucane, pectine, tamarindus indica seed polysaccharide and hyaluronic acid. In an even more preferred embodiment the the method is used for the productions of biopolymers with defined average molecular weight selected from sodium alginate or hyaluronic acid. In the most preferred embodiment the method is used for the production of hyaluronic acid with a defined average molecular weight.

In another aspect of the invention, the invention relates to a method for the production of compositions, comprising a biopolymer, wherein the biopolymer has a defined average molecular weight, the method comprising:
(i) providing a base composition comprising a biopolymer,
(ii) lyophilizing said composition;
wherein the temperature maximum during the lyophilization process is selected to facilitate a controlled and defined degradation of the biopolymer.

The inventors found that the present invention is suitable for the production of compositions, comprising biopolymers. These compositions comprise a biopolymer with defined average molecular weight and other optional components, such as dermatological, pharmaceutical or cosmetic ingredients and just need to be emulsified or dissolved to be used.

In one embodiment of the invention the maximum temperature during the sublimation process is selected from the range of −40° C. to 150° C. In a preferred embodiment the temperature is selected from the rage of 0 to 140° C. In a more preferred embodiment the temperature is selected from the range of 60 to 130° C. In the most preferred embodiment the temperature is 120° C.

In an alternative embodiment the temperature during the sublimation process is varied during the lyphilization process. In a preferred first embodiment the sublimation is carried out at two temperatures. A preferred temperature profile is shown in FIG. 3.

In one embodiment of the invention the sublimation process is carried out at two different temperatures. Preferably the first temperature is selected from the range of −40° to +40° C. and the second temperature is selected from the range of 60 to 130° C. In a preferred embodiment the first temperature is selected from the range of −20 to 20° C. and the second temperature is selected from the range of 80 to 120° C. In a most preferred embodiment the first temperature is 10° C. and the second temperature is 120° C.

In one embodiment of the invention the pressure during the sublimation step is between 50 μbar and 800 μbar. In a preferred embodiment of the invention the pressure is between 75 μbar and 600 μbar, more preferably between 100 μbar and 400 μbar, even more preferably between 150 μbar and 300 μbar. In a most preferred embodiment the pressure during the sublimation step is 200 μbar.

In one embodiment of this aspect of the invention the biopolymer in the compositions is selected from the group comprising hyaluronic acid, collagen, glucosamino glycans, polysaccharides and fucoidanes. In a more preferred embodiment the biopolymer is selected from the group consisting of alginates, rhizobian gum, sodium carboxy methyl cellulose, pullulan, Biosaccharide Gum-1, glucomannane, beta-glucane, pectine, tamarindus indica seed polysaccharide and hyaluronic acid. In an even more preferred embodiment the biopolymer is sodium alginate or hyaluronic acid. In the most preferred embodiment the biopolymer is hyaluronic acid.

In a preferred embodiment the biopolymer is a biopolymer with high molecular weight. In a more preferred embodiment the biopolymer is a biopolymer with native high molecular weight.

The composition comprising a biopolymer may comprise additional biopolymers or other polymers. Any composition is suitable, as long as the composition comprises additionally water.

In a preferred embodiment the base composition is an aqueous solution or an emulsion comprising a biopolymer.
In a more preferred embodiment the base composition comprises:
(i) the biopolymer,
(ii) water,
(iii) optionally one or more pharmaceutically, dermatologically and/or cosmetically acceptable compounds and/or oils,
(iv) optionally an emulsifying agent
(v) optionally additional pharmaceutically, dermatologically and/or cosmetically active components.

In alternative embodiments the base composition is a gel or a liquid with low to high viscosity.

The composition preferably contains further additional cosmetic, dermatological or pharmaceutical ingredients or additions. Non-limiting examples for these ingredients are emollients, cosmetically acceptable ingredients and dyes, perfumes or pharmaceutically active substances like panthenol.

Non limiting examples for said ingredients or additions are: skin conditioning agents, skin-smoothing agents, agents for skin hydration, e.g. panthenol or panthothenol, natural moisturising factors, such as glycerine, lactid acid or urea. Alternatively a physical or chemical sunscreens, keratolitics, such as α- or β-hydroxy acids, α- or β-ketoacids. Further possible ingredients include radical catchers, anti-ageing agents, vitamins or derivatives thereof, e.g. vitamin C (ascorbic acid) or esters or glycosides thereof, antioxidants, such as catechins or flavonoids.

Further potential ingredients comprise resveratrol, gluthation, ferulic acid, Q10, polyphenols, ceramides, saturated and or unsaturated fatty acids and there glycerides. Furthermore esters, such as wax esters, such as jojoba oil, triglycerides in general (neutral oil, argan oil, shea butter) or unsaponifiable components from plant oils.

Further polysaccharides of vegetable, biotechnological or marine origin, as well as their hydrolysates. Other ingredients might include enzymes, e.g. bromelain, coenzymes, enzyme inhibitors, amino acids, natural and synthetic oligopeptides, peptides such as collagen and elastin, as well as their hydrolysates, neuropeptides, growth factors, alcaloids. In some embodiments the ingredients optionally include phytopharmaca such as aescin, ginsenosides, ruscogenine or aloin. Further polymers are alginates, cellulose derivatives, starch, chitosan, chondroitin sulfate, further synthetic biopolymers with biological function or compatibility Non-limiting examples of cosmetic additions comprise skin lightening agents, inorganic or synthetic fillers or decorative substances, such as coloring pigments or dyes or particles. Some embodiments of the invention comprise substance for the cosmetic beautification of eyes, lips or face.

In some embodiments the composition further comprises therapeutically active agents, such as anti-acne or anti-rosacea agents, antimicrobial agents, such as silver and it's derivatives, iodine or PVP-iodine, antiperspirants, pain relieving substances such as lidocain or ibuprofen, adstringent substances, deodorizing compounds, antiseborrhoeic substances or antiseptics. Furthermore cells or cell components, such as autologous cells, allogenic cells, stem cells or platelet-rich plasma (PRP).

The composition preferably contains other ingredients, e.g. stabilizers, preserving agents, to control the final parameters of the product, such a solubility or emulsifiability, mechanical stability, product viscosity or haptics.

In a particular embodiment of the present invention the base composition is prepared and provided in an appropriate container, which is suitable for the freezing and lyophilization process, as well as optionally able to serve as packaging for the lyophilized composition comprising a biopolymer with defined average molecular weight.

The invention further relates to the use of said method for the production of compositions comprising a biopolymer with defined average molecular weight and to compositions comprising biopolymers produced according to a method of the present invention.

In one embodiment of the present invention the final composition can serve as a basis for aqueous liquids, emulsions with low viscosity, serum-like liquids, masks, creams, cream masks, patches or segments for topical applications.

FIGURE LEGENDS

FIG. 1: Correlation of average molecular weight, skin penetration and biological activity of hyaluronic acid.

FIG. 2: Correlation of pH, temperature and obtained average molecular weight obtained, when processing a composition comprising hyaluronic acid according to the present invention.

FIG. 3: Overview of suggested temperature profiles over time during the lyophilization process.

Figure 4:
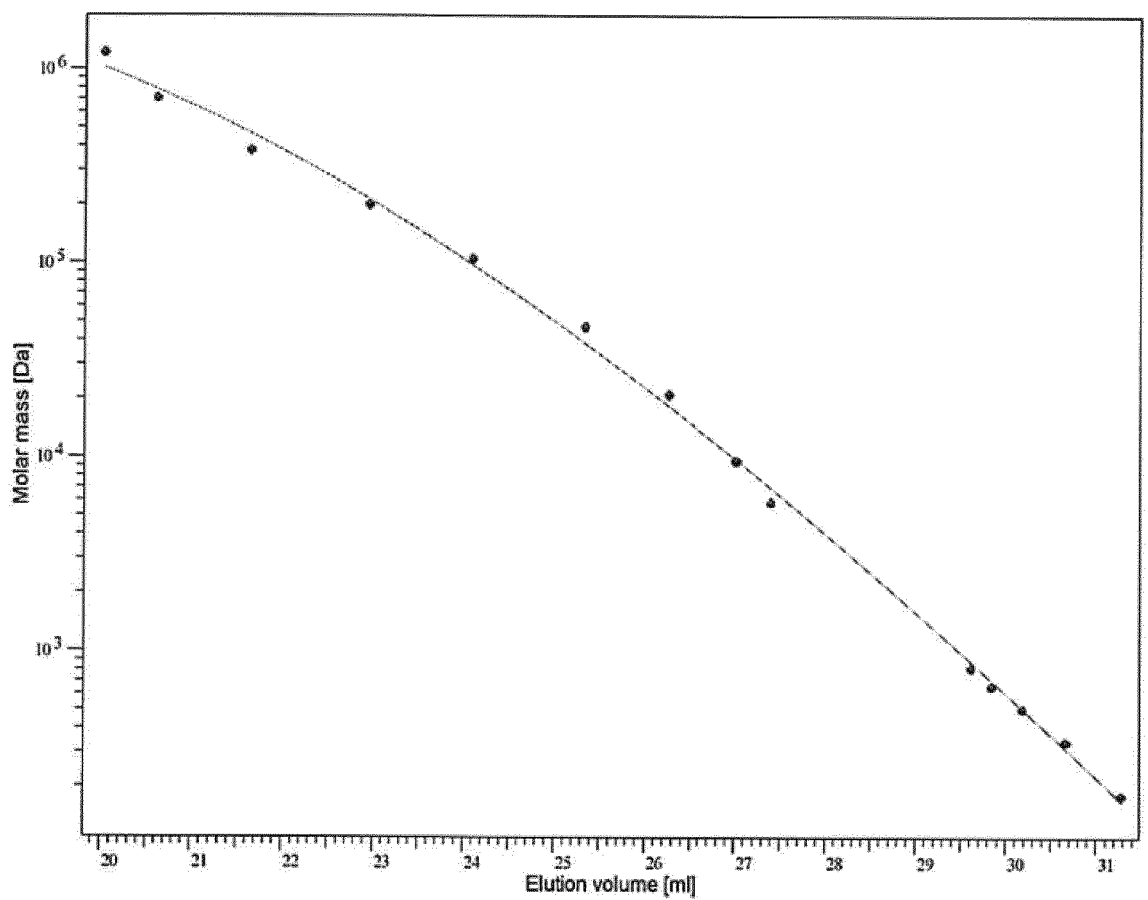

FIG. 4: Calibration curve to determine average molecular weight of hyaluronic acid, processed according to the present invention.

Figure 5:
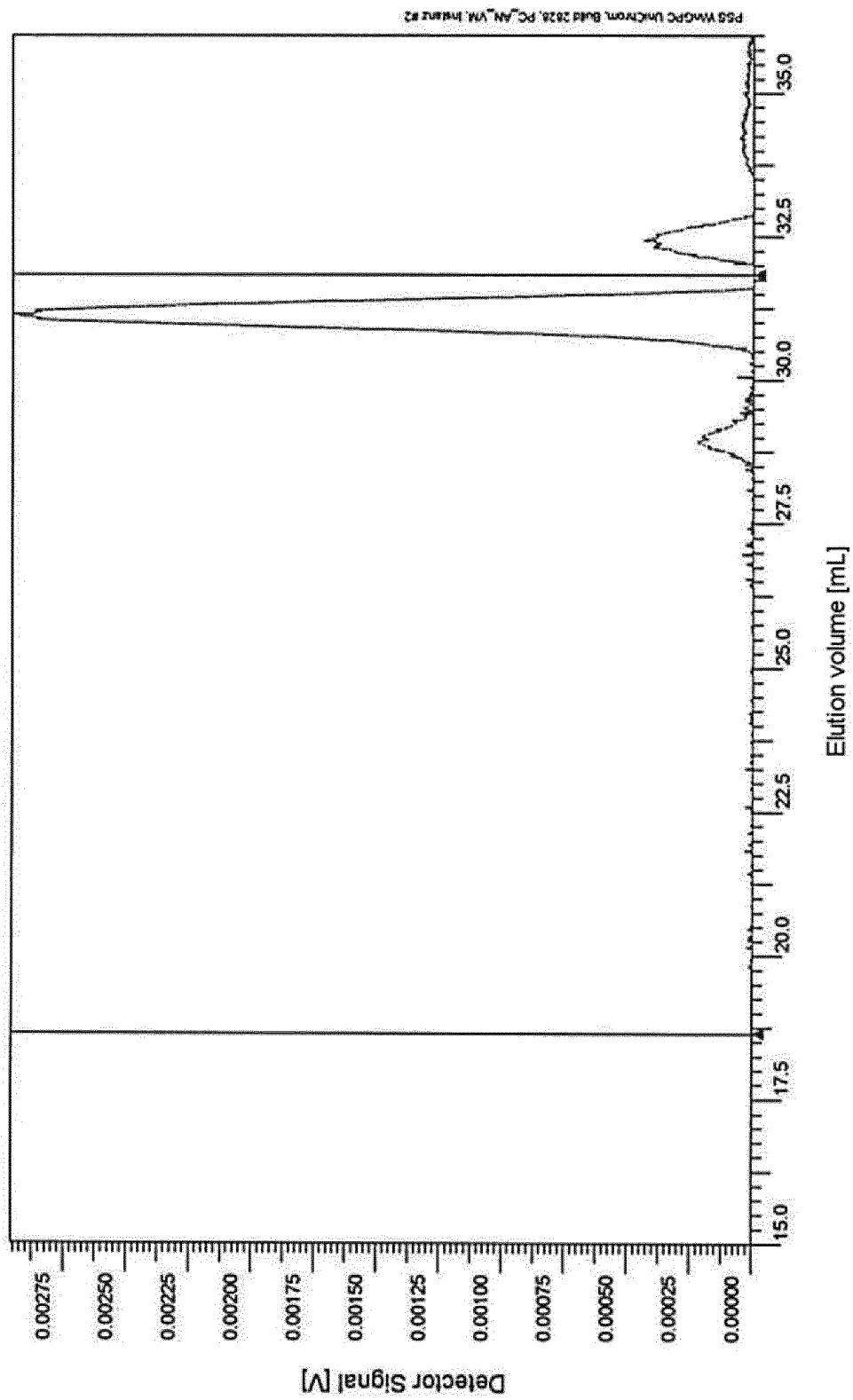
Figure 5:
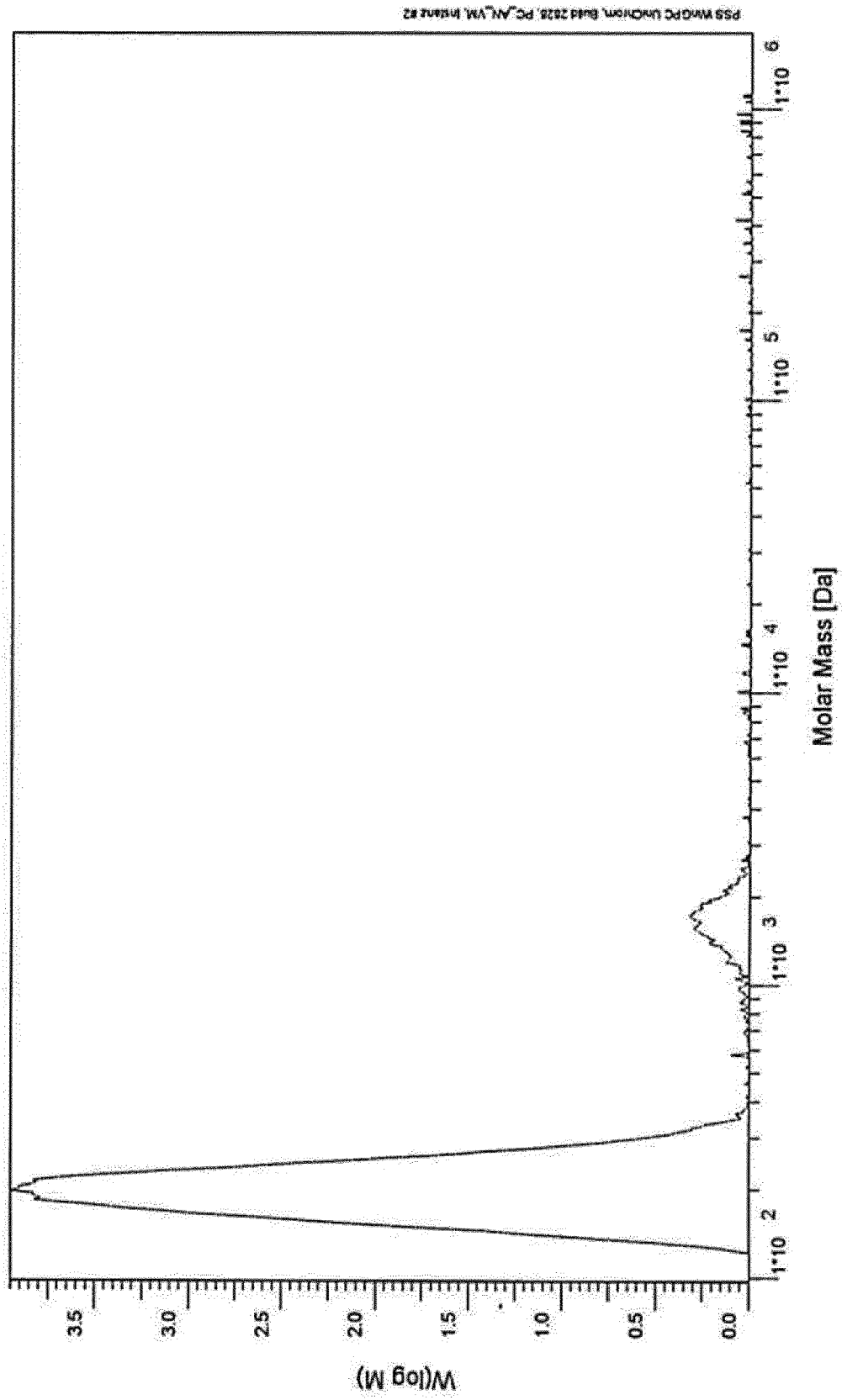
Figure 5:
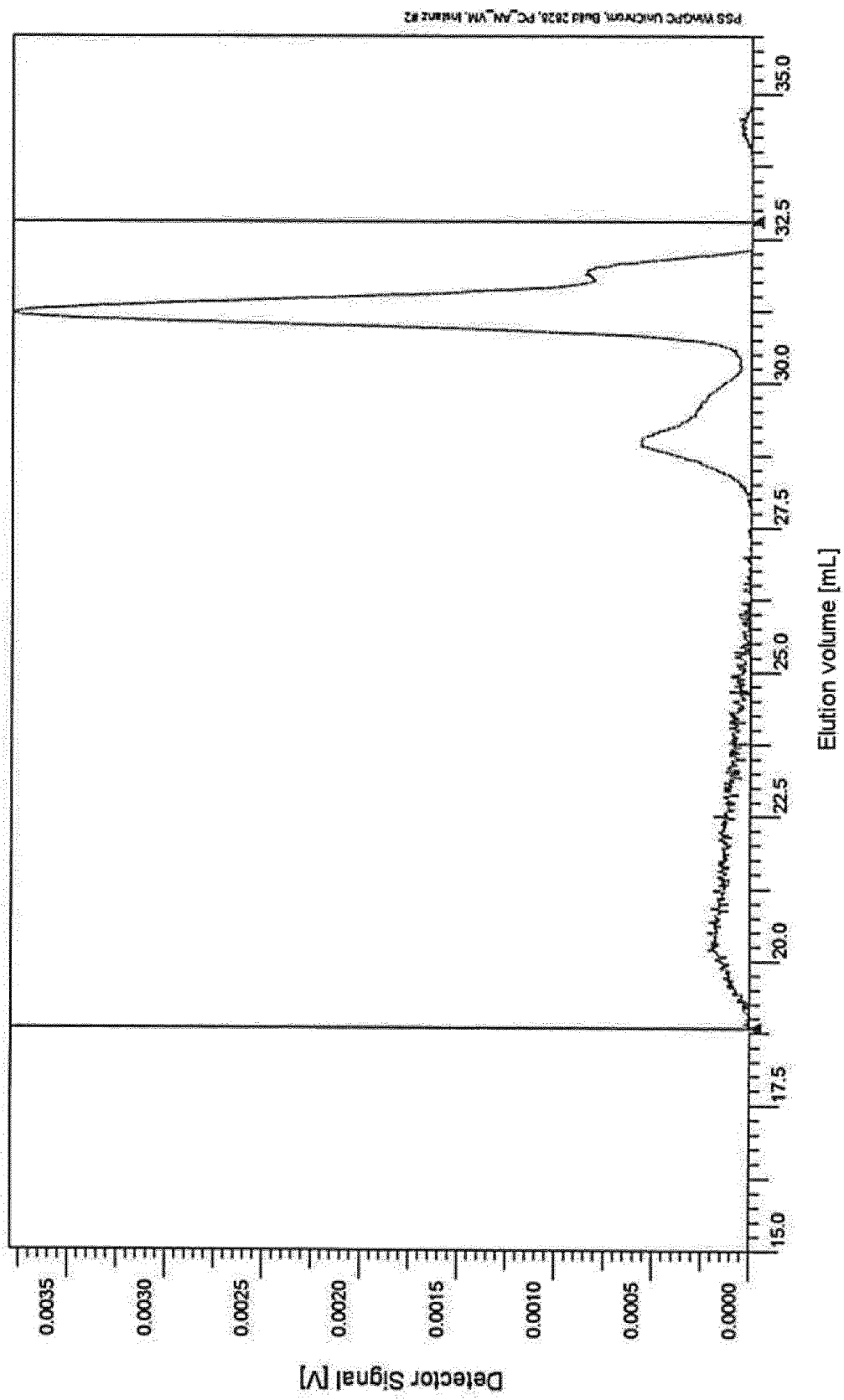
Figure 5:
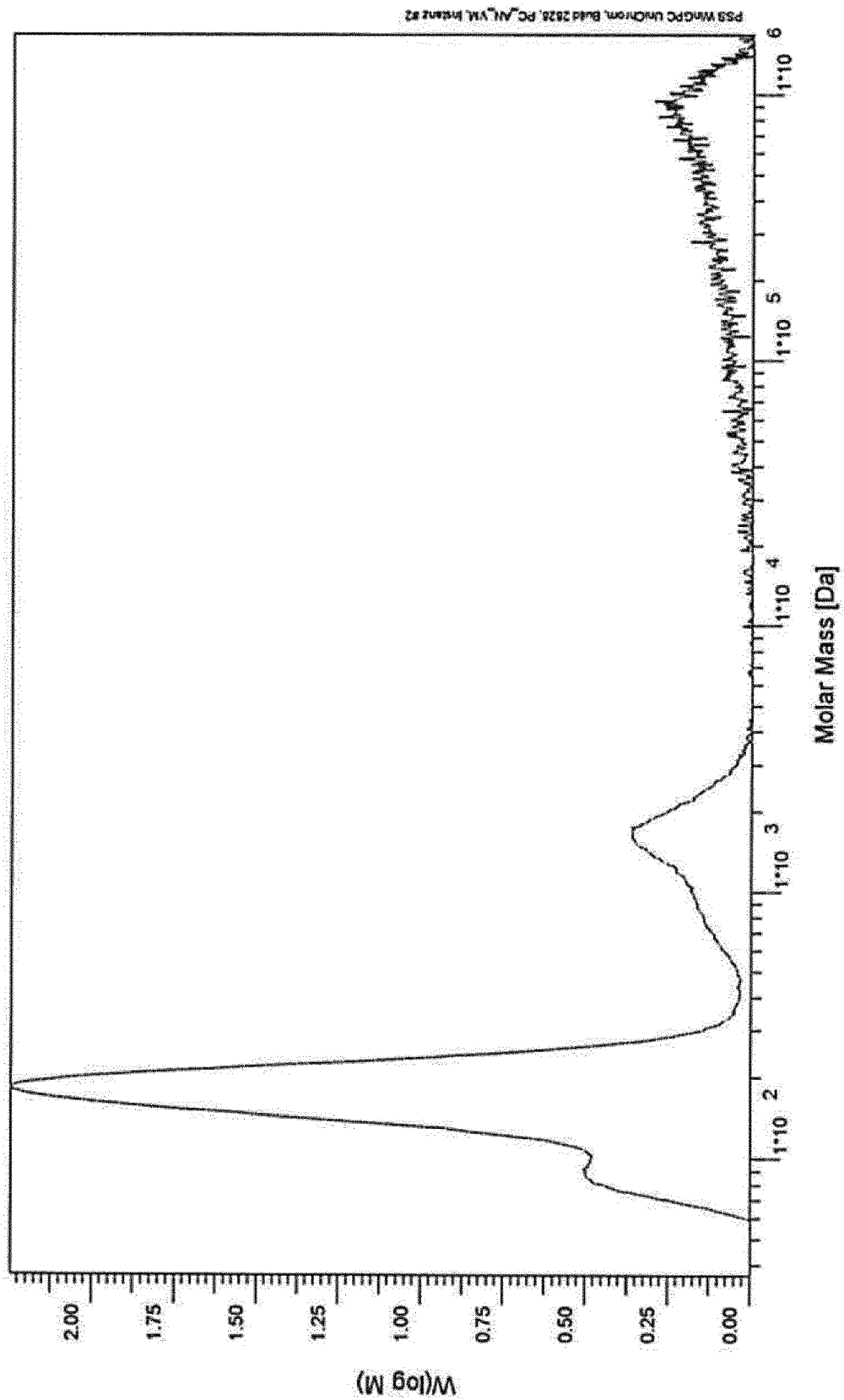

FIG. 5: Elugram and molecular mass profiles of neutral oil (5A) and Sepinov EMT-10 (5B) processed according to the present invention.

Figure 6:
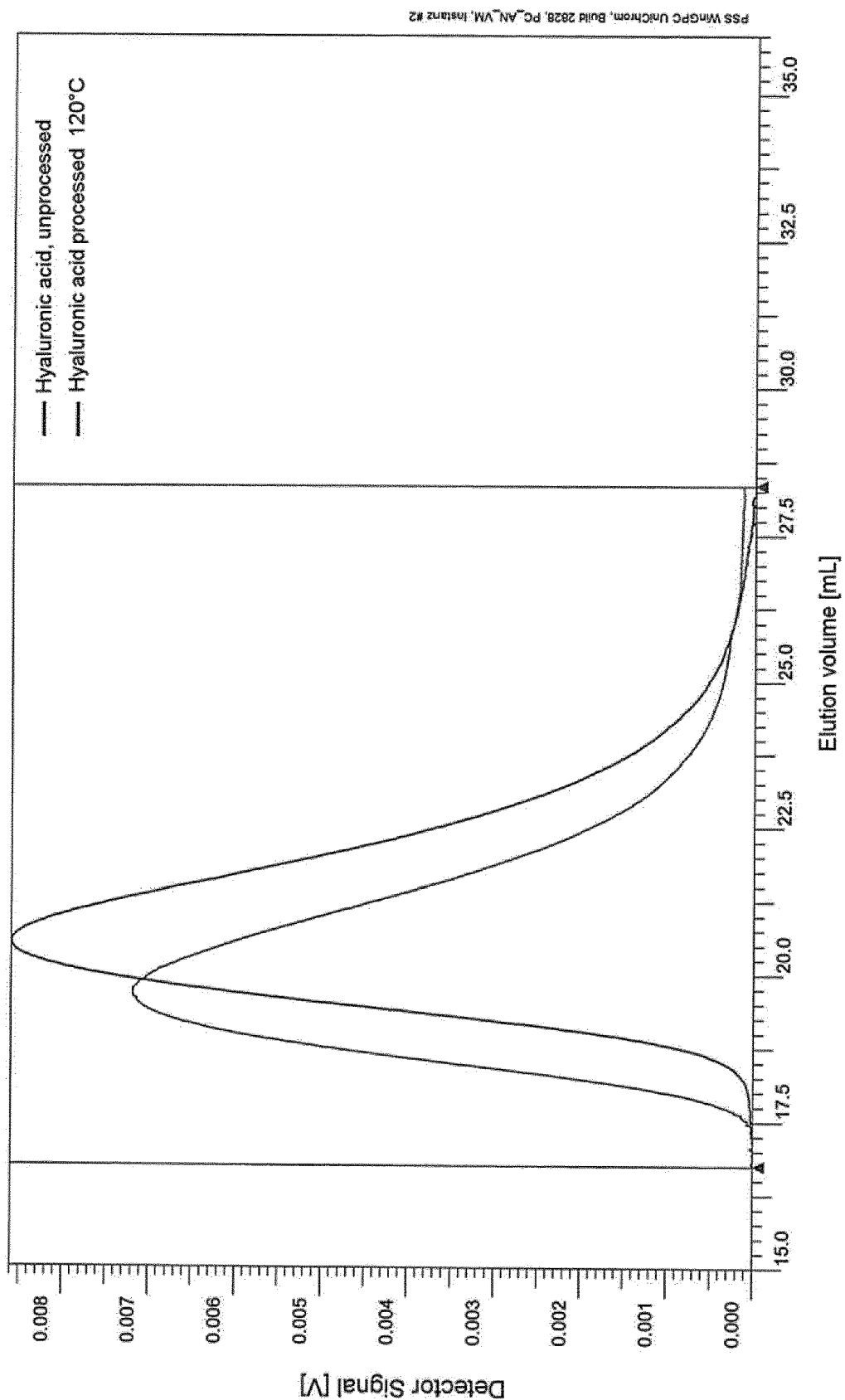
Figure 6:
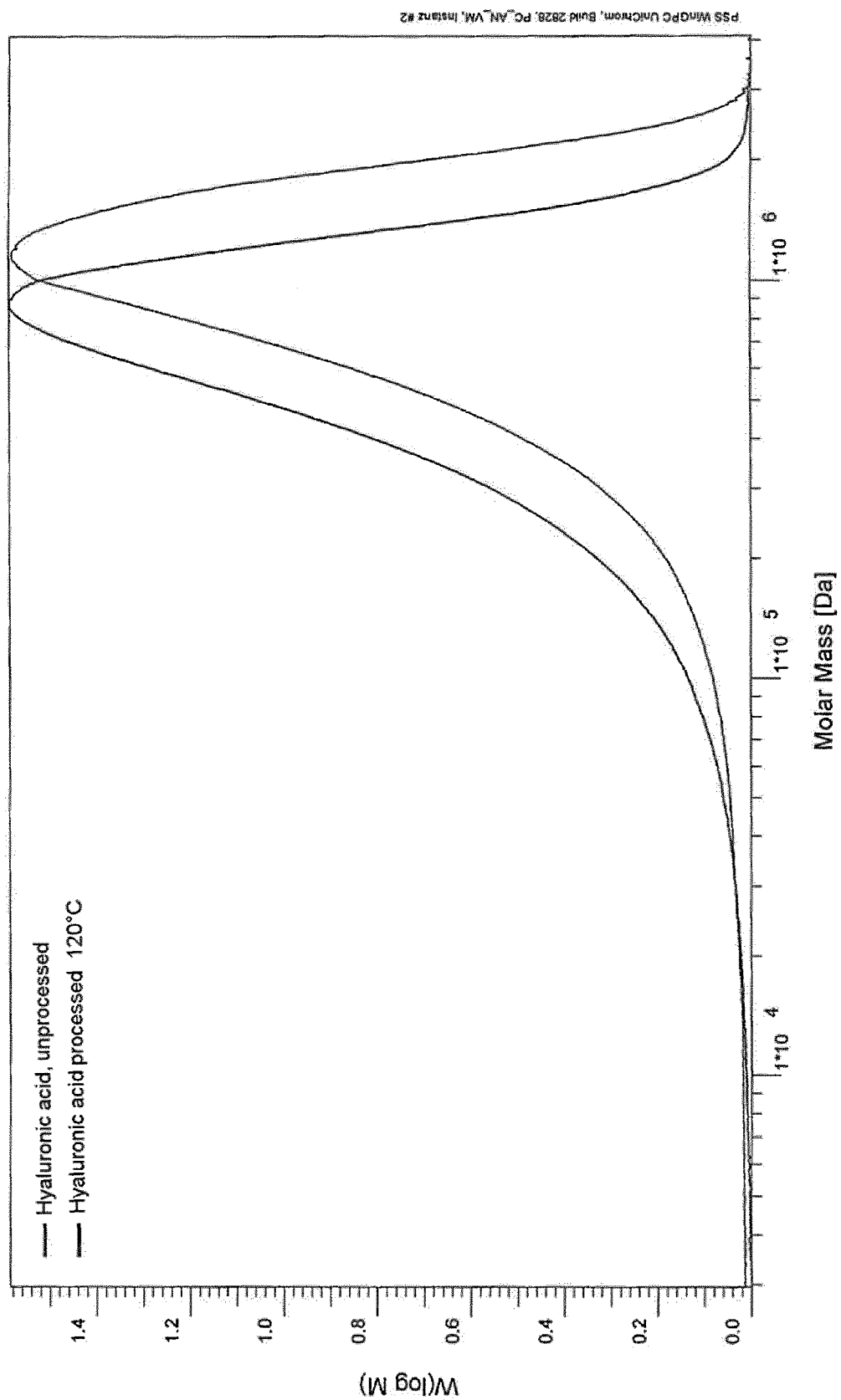

FIG. 6: comparison of the elution profiles (6A) and molecular mass profiles (6B) of native hyaluronic acid and hyaluronic acid, lyophilized 120° C.

Figure 7:
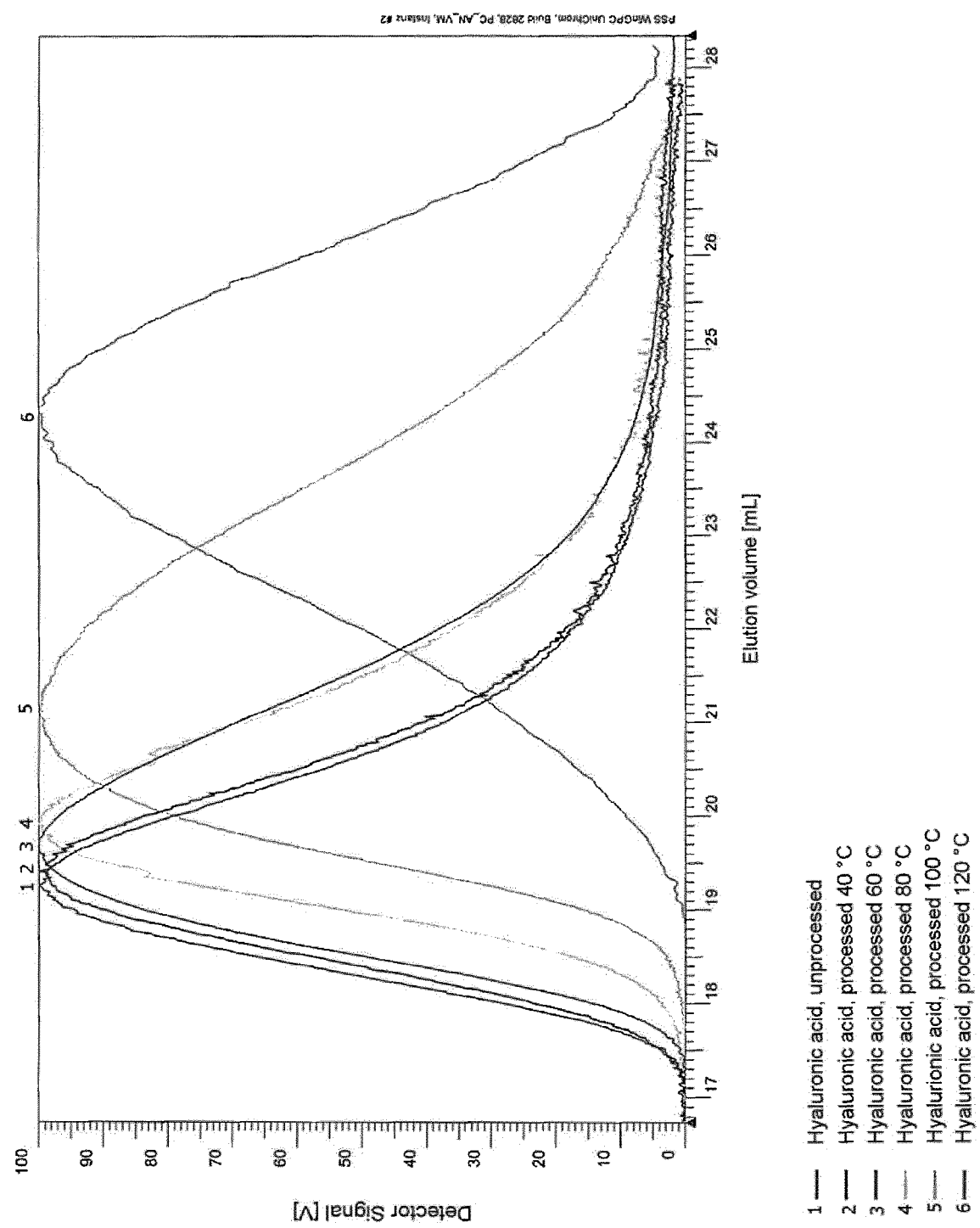
Figure 7:
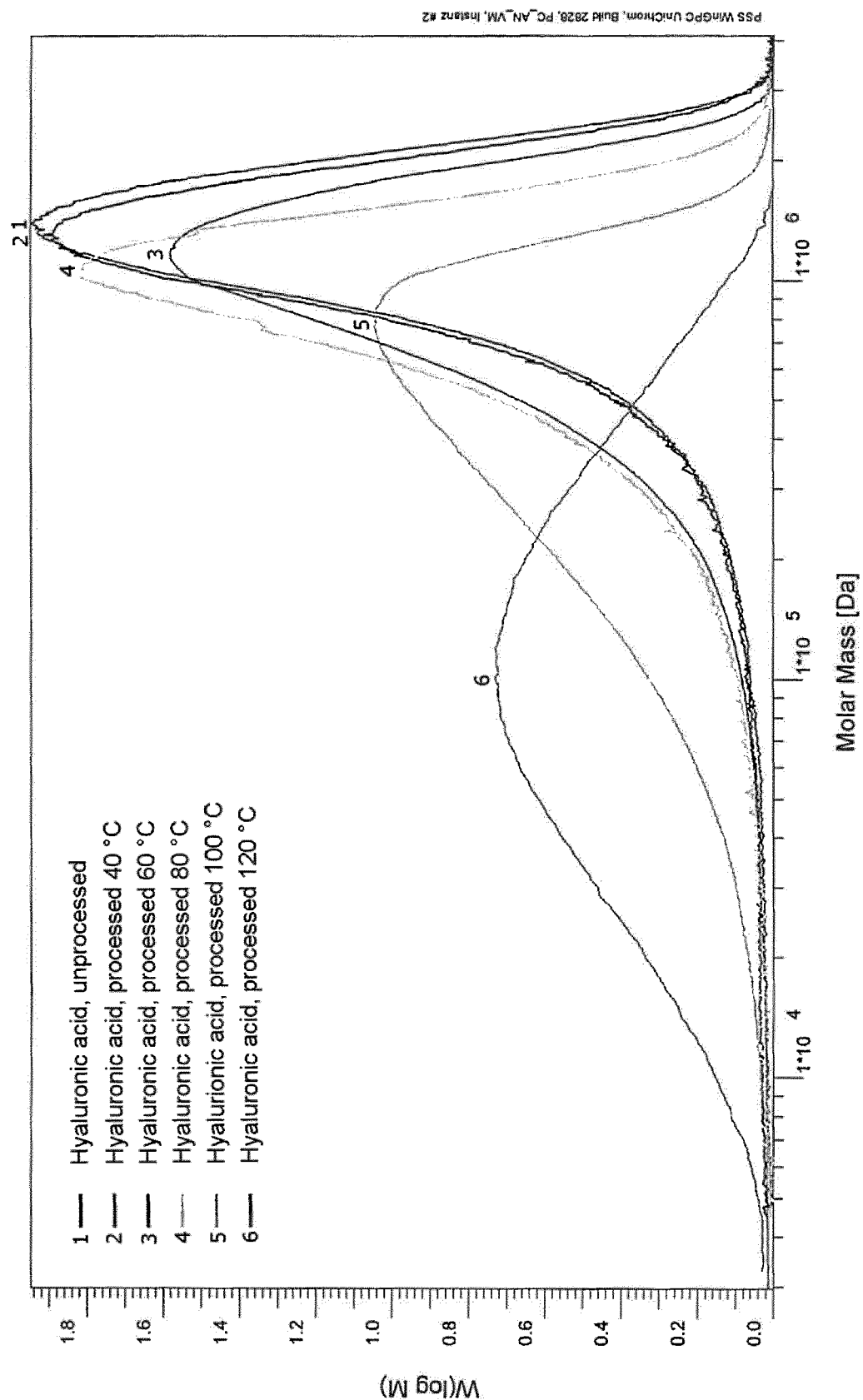

FIG. 7: Comparison of the elution profile (7A) and molecular mass profiles (7B) a mixture of hyaluronic acid, Sepinov EMT-10 and neutral oil, lyophilized at different temperatures.

Figure 8:
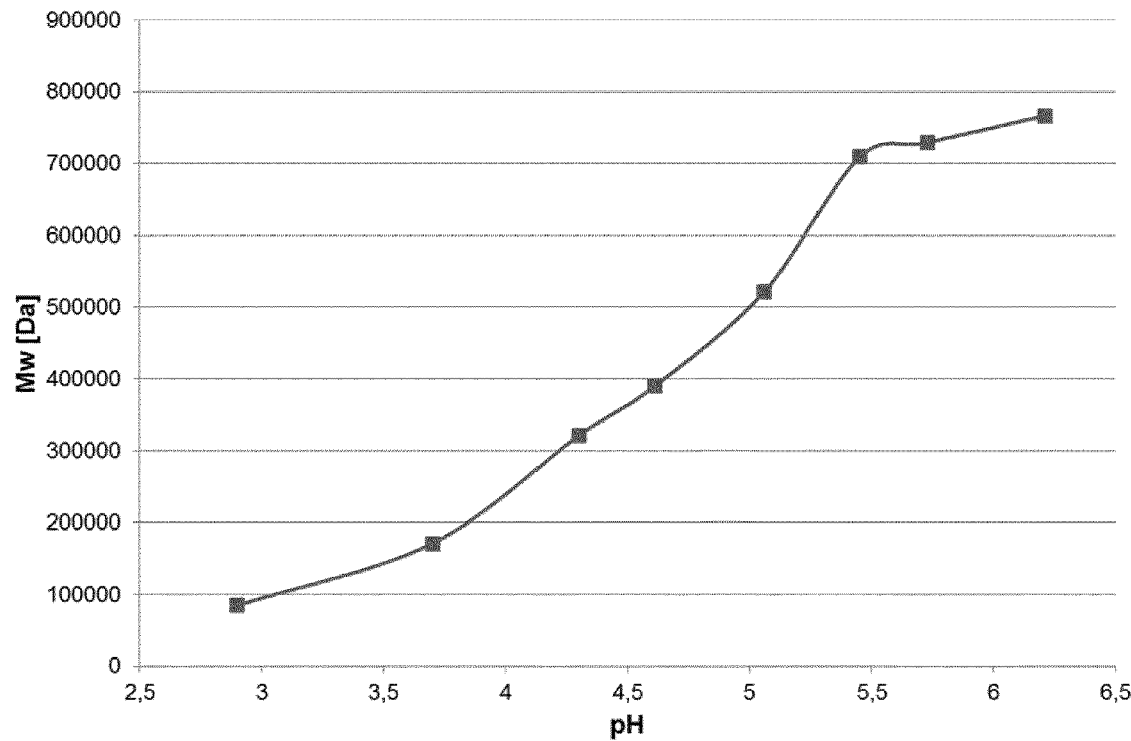

FIG. 8: Molecular weight of lyophilized samples of 1 wt-% high molecular weight HA samples with pH adjusted in the range of 6.21 to 2.9.

Figure 9:
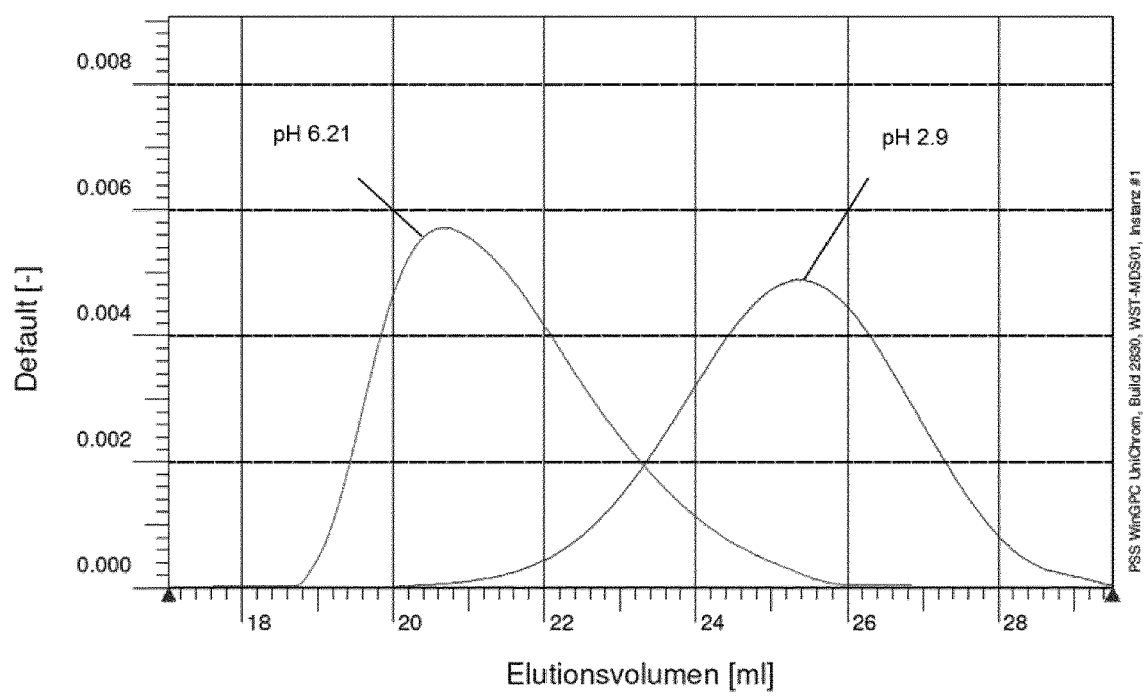

FIG. 9: Molecular weight distributions of lyophilized samples of 1 wt-% high molecular weight HA samples with pH adjusted to 6.21 and 2.9.

Figure 10:
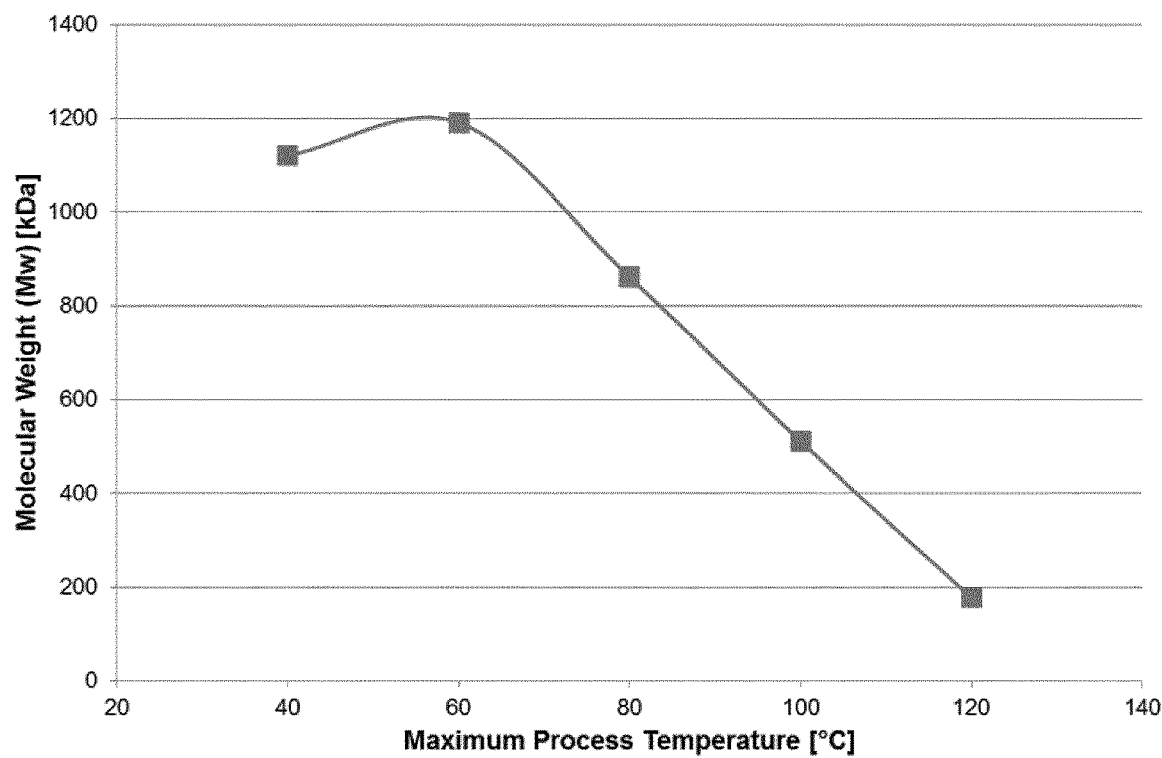

FIG. 10: Molecular weight of hyaluronic acid containing emulsions lyophilized at different process temperatures.

EXAMPLES

Example 1

Controlled Degradation of Hyaluronic Acid

Deionized water is transferred to 1 l lab reactor and stirred at 75° C. Hyaluronic acid powder is added and stirred at 75° C. at 700 rpm for 15 min until the material is dissolved. The emulsifier component is added and stirred at 50° C. for 15 min at 1400 rpm under reduced pressure (200 μbar). The oil component is added and stirred at 1400 rpm/45° C./200 μbar for 10 min and subsequently for 5 min at 2100 rpm/45° C./200 μbar. The received emulsion is cooled to room temperature and transferred to 10 ml glass vials and stored overnight at ambient conditions. Samples were frozen in a deep freezer for minimum 16 h and subsequently lyophilized up to maximum target temperature.

As a proof of principle hyaluronic acid was processed according to the invented method. Herein, pure hyaluronic acid, and compositions of hyaluronic acid with MCT neutral oil and Sepinov EMT-10 were lyophilized at varying temperatures.

The following samples were analyzed:
1. Neutral oil, unprocessed
2. Sepinov EMT-10, unprocessed
3. Hyaluronic acid, unprocessed
4. Sepinov EMT-10, lyophilized at 120° C.
5. Hyaluronic acid, lyophilized at 120° C.
6. Mixture (hyaluronic acid, neutral oil and Sepinov EMT-10), lyophilized at 40° C.
7. Mixture, lyophilized at 60° C.
8. Mixture, lyophilized at 80° C.
9. Mixture, lyophilized at 100° C.
10. Mixture, lyophilized at 120° C.

The samples were analyzed using size exclusion chromatography on an HPLC system, using 3 analytical columns. Samples were dissolved in PBS-Buffer with pH 7.4, non-soluble parts were removed by filtration.

The columns were calibrated using dextran/pullulan standards. Molecular masses of the samples were determined based on the said calibration (for the calibration curve see FIG. 4).

Only pure hyaluronic acid samples were completely soluble. The soluble components of the Sepinov EMT-10 or neutral oil, do not produce any problematic signals during analysis (see FIGS. 5a and b).

The results clearly show that the composition and the lyophilization temperature affect the average molecular weight of the hyaluronic acid. While an effect of lyophilization on pure hyaluronic acid at high temperatures occurs and results in a reduced average molecular weight (see FIG. 6a,b), the effect is stronger in the mixtures (see FIG. 7a,b).

Overall it is clearly visible that the choice of parameters during the lyophilization process is suitable to control the average molecular weight of hyaluronic acid after the lyophilization.

Example 2

Influence of the pH-value on Degradation

Hyaluronic acid with a molecular weight of 1.478 Mio Da (Contipro, Mw, according to gel permeation chromatography) was dissolved in 1 wt-% solution in distilled water at 80° C. for five minutes. The pH was adjusted with hydrochloric acid in the range of 2.9 to 6.21.

7.5 ml HA solution was dispensed in 10 ml glass vials, samples were frozen at −20° C. overnight and placed in a Christ Epsilon 2-10D LSC plus HT device and processed for approximately 20 hours according to the 10/120° C. temperature profile shown in FIG. 3.

Lyophilised samples were diluted in GPC buffer (pH 7.4) at a concentration of 0.3 wt-% and analyzed by means of gel permeation chromatography against Pullulan and Dextran molecular weight standards.

Independent on adjusted pH, all samples were cleaved showing a maximum of 766 kDa at pH 6.21 and a minimum 84.75 kDa at pH 2.9 (FIG. 7). The higher the amount of free acid functionality in the polymer, the higher the tendency of the polymer to be cleaved. A corresponding elugram of the high as well as the low molecular weight sample is shown in FIG. 8.

Example 3

Degradation of Hyaluronic Acids with Different Molecular Weights

Four differents types of hyaluronic acid (Contipro/GfN 3010 (MW: 1478 kDa), Principium Cube3 (MW: 733 kDa), Principium Signal-10 (MW: 25 kDa) and Freda mini-HA (MW: 27 kDa)) were dissolved in 1 wt-% solution in distilled water at 80° C. for five minutes. Solutions were used as is or pH was adjusted to approximately 3.5.

7.5 ml HA solution was dispensed in 10 ml glass vials, samples were frozen at −20° C. overnight and placed in a Christ Epsilon 2-10D LSC plus HT device and processed for approximately 20 hours according to the 10/120° C. or alternatively the 120° C. temperature profile shown in FIG. 3.

Lyophilised samples were diluted in GPC buffer (pH 7.4) at a concentration of 0.3 wt-% and analysed by means of gel permeation chromatography against Pullulan and Dextran molecular weight standards.

High and medium molecular weight HAs showed a moderate decay of molecular weight at original pH dissolved in distilled water, whereas molecular weight of substances decayed drastically at low pH, as shown in the following table.

| Mw [kDa] non-processed | pH | Mw [kDa]* processed at 10/120° C. | Mw [kDa]* processed at 120° C. |
| --- | --- | --- | --- |
| 1478 | 6.11 | 594 | 531 |
| 1478 | 3.50 | 97 | 68 |
| 733 | 6.63 | 331 | 297 |
| 733 | 3.57 | 97 | 78 |
| 25 | 3.36 | 23 | 21 |
| 27 | 6.53 | nd | 29 |
| 27 | 3.50 | nd | 28 |

Example 4

Emulsions Containing Hyaluronic Acid 5 g of high molecular weight hyaluronic acid (GfN/Contipro 3010, 1.5 MDa) was dissolved in 465 g of distilled water, heated to 80° C. and stirred by means of a Somakon MP-LB (1 l) mixing device at 1400 rpm and ambient pressure for 15 minutes.

7.5 g Sepinov EMT-10 (INCI name: Hydroxyethyl acrylate (and) Sodium Acryloyl Dimethyl Taurate Copolymer) was added the pH was adjusted to 3.05 and mixture was stirred at 1400 rpm/200 μbar for further 15 minutes at 80° C.

25 g of medium chain triglyciderides (MCTs) as model oil compound were added and homogenized at 2100 rpm/200 μbar for 5 minutes.

7.5 ml of the resulting emulsion was dispensed in 10 ml glass vials, samples were frozen at −20° C. overnight and placed in a Christ Epsilon 2-10D LSC plus HT device and processed for approximately 20 hours at maximum 40, 60, 80, 100 and 120° C.

Lyophilised samples were diluted in GPC buffer (pH 7.4) at a concentration of 0.3 wt-% and analyzed by means of GPC. FIG. 9 shows the temperature dependence of the molecular weight (Mw) of the hyaluronic acid decreasing with increasing maximum process temperature.

Example 5

Lyophilization of Different Biopolymers

Polymers were dissolved in 1 wt-% solution in distilled water at 80° C. for five minutes. The pH of the solutions was measured and the molecular weight distribution of the non-processed polymer solutions were determined by means of size exclusion chromatography against Pullulan and Dextran molecular weight standards diluting the samples to 0.3 wt-% in PBS buffer (pH 7.4).

7.5 ml polymer solution was dispensed in 10 ml glass vials, samples were frozen at −20° C. overnight and placed in a Christ Epsilon 2-10D LSC plus HT device and processed for approximately 20 hours according to the 10/120° C. temperature profile shown in FIG. 3.

Lyophilised samples were diluted in GPC buffer (pH 7.4) at a concentration of 0.3 wt-% and analysed by means of GPC. The results are shown in the following tables.

Sodium alginates:

| Mw [kDa]* non-processed | pH | Mw [kDa] processed at 10/120° C. | Mw [kDa] processed at 120° C. |
| --- | --- | --- | --- |
| 1074 | 6.88 | 336 | 269 |
| 1074 | 3.50 | 239 | nd |
| 1020 | 7.03 | 472 | 336 |

-continued

| Mw [kDa]* non-processed | pH | Mw [kDa] processed at 10/120° C. | Mw [kDa] processed at 120° C. |
|---|---|---|---|
| 1020 | 3.50 | 287 | nd |
| 881 | 7.15 | 259 | 233 |
| 881 | 3.50 | 184 | nd |

Polysaccharides:

| Polymer | Monomers | pH | Mw [kDa]* non-processed | Mw [kDa]** processed at 10/120° C. | Mw [kDa]** processed at 120° C. |
|---|---|---|---|---|---|
| Rhizobian Gum | tbd | 5.59 | 706 | 533 | 592 |
|  |  | 3.50 | 706 | 354 | nd |
| Sodium carboxy methyl cellulose | Funktionalized glucose | 6.66 | 682 | 689 | 712 |
|  |  | 3.5 | 682 | 309 | 308 |
| Pullulan | Glucose (Maltotriose) | 5.46 | 314 | 239 | 278 |
|  |  | 3.50 | 314 | 61 | nd |
| Biosaccharide Gum-1 | Fucose | 7.35 | 2037**** | 1735**** | 1598**** |
|  |  | 3.50 | 2037**** | 443 | nd |
| Glucomannane | Glucose, mannose | 5.84 | 1304 | 1119 | 980 |
|  |  | 3.50 | 1304 | 247 | nd |
| Beta-Glucan (and) Pectin | Galacturonic acid, rhamnose | 4.02 | 778 | 389 | 358 |
| Tamarindus indica Seed Polysaccharide | Glucose, xylose, galoctoxylose | 6.20 | 956 | 933 | 927 |
|  |  | 3.50 | 956 | 602 | nd |

Example 6

Lyophilisation of a Hyaluronic Acid Emulsions Containing Different Emulsifying Polymer Components 3 g of high molecular weight hyaluronic acid (GfN/Contipro 3010, 1.5 MDa) was dissolved in 277.5 g of distilled water heated to 80° C. and stirred by means of a Somakon MP-LB (1 l) mixing device at 1400 rpm and ambient pressure for 15 minutes.

4.5 g emulsifying polymer was added and the pH was adjusted to approximately 3 and mixture was stirred at 1400 rpm/200 mbar for further 15 minutes at 80° C.

15 g of medium chain triglyciderides (MCTs) were added and homogenized at 2100 rpm/200 mbar for 5 minutes.

7.5 ml of the resulting emulsions was dispensed in 10 ml glass vials, samples were frozen at −20° C. overnight and placed in a Christ Epsilon 2-10D LSC plus HT device and processed for approximately 20 hours at maximum 120° C.

The following table shows the emulsifying polymer used, the pH values as well as the viscosity of the emulsion (measured with a hand-held HAAKE Viscotester 2 plus) prior to lyophilisation. All freeze-dried samples provided fast rehydration to opaque emulsions.

| Emulsifying Polymer | Manufacturer | INCI name | pH | Viscosity* [Pas] |
|---|---|---|---|---|
| EMT-10 | SEPPIC | Hydroxyethyl acrylate (and) Sodium Acryloyl Dimethyl Taurate Copolymer | 3.05 | 15 |
| P-88 | SEPPIC | Hydroxyethyl acrylate (and) Sodium Acryloyl Dimethyl Taurate Copolymer | 3.06 | 14.2 |
| Bergamuls | Berg& Schmidt | Beta-Glucan (and) Pectin | 3.03 | 6.2 |

Example 7

Lyophilisation of a Hyaluronic Acid Emulsions Containing Different Oil Components 3 g of high molecular weight HA (GfN/Contipro 3010, 1.5 MDa), 277.5 g of distilled water, 4.5 g EMT-10 as well as 15 g of oil component (MCT (Cosnaderm), Marula Oil (Seatons), Jojobaoil (J. H. Müller GmbH) or Argan oil (Seatons)) were processed as described in example 6.

7.5 ml of the resulting emulsions was dispensed in 10 ml glass vials, samples were frozen at −20° C. overnight and placed in a Christ Epsilon 2-10D LSC plus HT device and processed for approximately 20 hours at maximum 120° C. All freeze-dried samples provided fast rehydration resulting in opaque emulsions.

Example 8

Lyophilisation of a Hyaluronic Acid Emulsions Containing a UV Filter Blend 3 g of high molecular weight hyaluronic acid (GfN/Contipro 3010, 1.5 MDa) was dissolved in 277.5 g of distilled water heated to 80° C. and stirred by means of a Somakon MP-LB (1 l) mixing device at 1400 rpm and ambient pressure for 15 minutes. 4.5 g Sepinov EMT-10 was added and mixture was stirred at 1400 rpm/200 mbar for further 15 minutes at 80° C.

6 g Eusolex 9010 (Avobenzone), 15 g Eusolex OCR (Octocrylene) and 7.5 g Eusolex OR (Ethylhexyl Salicylate) were dissolved in 15 g of medium chain triglyciderides (MCTs) and the UV filter mixture was added to the polymer solution and homogenized at 2100 rpm/200 mbar for 5 minutes.

7.5 ml of the resulting emulsions was dispensed in 10 ml glass vials, samples were frozen at −20° C. overnight and placed in a Christ Epsilon 2-10D LSC plus HT device and processed at 10/120° C. as shown in FIG. 3. Lyophilised samples were diluted in GPC buffer (pH 7.4) at a concentration of 0.3 wt-% and analysed by means of GPC. Mw of the lyophilisate was measured as 975 kDa.

Example 9

Lyophilisation of a Hyaluronic Acid Emulsions Containing Microcrystalline Silver 3 g of high molecular weight hyaluronic acid (GfN/Contipro 3010, 1.5 MDa) was dissolved in 277.5 g of distilled water heated to 80° C. and stirred by means of a Somakon MP-LB (1 l) mixing device at 1400 rpm and ambient pressure for 15 minutes.

4.5 g Sepinov EMT-10 was added and mixture was stirred at 1400 rpm/200 mbar for further 15 minutes at 80° C. 700 mg of microcrystalline silver was dispersed in 15 g of medium chain triglyciderides (MCTs) and the mixture was added to the polymer solution and homogenized at 2100 rpm/200 mbar for 5 minutes.

7.5 ml of the resulting emulsions was dispensed in 10 ml glass vials, samples were frozen at −20° C. overnight and placed in a Christ Epsilon 2-10D LSC plus HT device and processed at 10/120° C. as shown in FIG. 3. All freeze-dried samples provided fast rehydration resulting in a colorless gel.

The invention claimed is:

1. A method of making a biopolymer having a defined average molecular weight, the method comprising:
   providing a composition comprising a biopolymer, wherein the biopolymer is selected from the group consisting of hyaluronic acid having a molecular weight of 1.5-0.025 MDa, collagen, glucosamino glycans, polysaccharides and fucoidanes; and
   lyophilizing the composition comprising the biopolymer to remove water from the composition by sublimation, and to facilitate a controlled and defined degradation of the biopolymer to form the biopolymer having the defined average molecular weight;
   (i) wherein the lyophilization process for hyaluronic acid having a molecular weight of 1.5-0.025 MDa occurs over two temperatures, wherein the first temperature is 10° C. and the second temperature is 120° C.; and
   wherein the composition prior to lyophilization has a pH value between 6.63 and 3.36 to facilitate the controlled and defined degradation of the hyaluronic acid to hyaluronic acid having the defined average molecular weight in a range between 594 kDa and 23 kDa,
   (ii) wherein the lyophilization process for collagen, glucosamino glycans, polysaccharides, and fucoidanes occurs over two temperatures, wherein the first temperature is 10° C. and the second temperature is 120° C., and wherein the composition prior to lyophilization has a pH value between 1.5 and 8.5 to facilitate the controlled and defined degradation of collagen, glucosamino glycans, polysaccharides, and fucoidanes to collagen, glucosamino glycans, polysaccharides, and fucoidanes, respectively, having the defined average molecular weight; and
   (iii) wherein the method does not comprise purifying the biopolymer having the defined average molecular weight after lyophilization.

2. The method according to claim 1, wherein the composition comprising the biopolymer is an aqueous solution or an emulsion.

3. The method according to claim 1, wherein the biopolymer produced is a pharmaceutically, dermatologically or cosmetically acceptable biopolymer.

4. A method of making a composition, comprising hyaluronic acid having a defined average molecular weight, the method comprising:
   (i) providing a base composition comprising hyaluronic acid having a molecular weight of 1.5-0.025 MDa, wherein the base composition has a pH between 6.63 and 3.36; and
   (ii) lyophilizing said base composition over two temperatures, wherein the first temperature is 10° C. and the second temperature is 120° C., and wherein the method facilitates a controlled and defined degradation of hyaluronic acid to form hyaluronic acid having the defined average molecular weight in a range between 594 kDa and 23 kDa.

5. The method according to claim 4, wherein the base composition is an emulsion or an aqueous solution.

6. The method according to claim 5, wherein the base composition is an emulsion comprising:
   (i) hyaluronic acid having a molecular weight of 1.5-0.025 MDa,
   (ii) water,
   (iii) a pharmaceutically, dermatologically or cosmetically acceptable oil,
   (iv) an emulsifying agent and
   (v) one or more emollients.

7. The method according to claim 6, wherein the base composition further comprises dermatological, pharmaceutical or cosmetic ingredients.

8. The method according to claim 4, wherein the base composition comprises additional components, so that the resulting lyophilized product is dissolvable or emulsifiable.

9. The method according to claim 4, wherein the composition produced is a pharmaceutically, dermatologically or cosmetically acceptable composition.

* * * * *